United States Patent [19]

Bihari et al.

[11] Patent Number: 4,888,346
[45] Date of Patent: Dec. 19, 1989

[54] METHOD FOR THE TREATMENT OF PERSONS INFECTED WITH HTLV-III (AIDS) VIRUS

[76] Inventors: Bernard Bihari, 29 W. 15th St.; Finvola Drury, 147 W. 22nd St., both of, New York, N.Y. 10011

[21] Appl. No.: 129,862

[22] Filed: Dec. 4, 1987

Related U.S. Application Data

[63] Continuation of Ser. No. 916,180, Oct. 7, 1986, abandoned.

[51] Int. Cl.$^4$ .............................................. A61K 31/44
[52] U.S. Cl. .................................................... 514/282
[58] Field of Search ........................................ 514/282

[56] References Cited

U.S. PATENT DOCUMENTS

| | | | |
|---|---|---|---|
| 3,773,955 | 11/1973 | Pachter et al. | 514/282 |
| 4,181,726 | 1/1980 | Bernstein | 514/282 |
| 4,217,353 | 8/1980 | Smith, Jr. | 514/282 |
| 4,267,182 | 5/1981 | Holaday | 514/282 |
| 4,434,168 | 2/1984 | Holaday | 514/282 |
| 4,464,378 | 8/1984 | Haussain | 514/282 |
| 4,546,103 | 10/1985 | Huebner | 514/282 |

*Primary Examiner*—Jerome D. Goldberg
*Attorney, Agent, or Firm*—William J. Daniel

[57] ABSTRACT

A treatment method for humans infected with HTLV-III (AIDS) virus, including patients clinically diagnosed as suffering from AIDS, those suffering from AIDS-related complex (ARC) as distinguished from AIDS itself, those exhibiting a positive serum test from AIDS virus coupled with a significant measurable diminution in immunological function, and those simply showing a positive serological test for the AIDS virus without other symptomatic indications, involves the administration, preferably orally where appropriate, of a small but effective amount in the range corresponding to about 1.0–5.0 mg per day for naltrexone, of an opiate receptor antagonist which at the indicated levels exhibits substantially antagonistic or blocking action exclusively upon Mu opiate receptors. The treatment appears from clinical data to impart substantially increased resistance against further progression of the disease beyond its original stage as well as to achieve significant symptomatic relief and clinical protection against serious further deterioration in condition in a predominant number of the patients treated, and appears further to have the ability to repair significantly existing damage to the patient's immunological system. Best results are obtained when the opiate antagonist is administered during the evening or early morning hours as contrasted with daylight or the working times, thereby enhancing the production by the body of endorphins which occurs optimally during such hours.

7 Claims, No Drawings

METHOD FOR THE TREATMENT OF PERSONS INFECTED WITH HTLV-III (AIDS) VIRUS

This application is a continuation of application Ser. No. 916,180, filed Oct. 7, 1986, now abandoned.

FIELD OF THE INVENTION

This invention relates to the treatment of persons infected with AIDS virus, technically referred to as HTLV-III virus, at various levels of severity of the infection and is also concerned with the treatment of persons suffering from natural or artificially induced immuno-deficient conditions.

BACKGROUND OF THE INVENTION

In April 1981, a new disease of awesome implications was identified and designated "acquired immune-deficiency syndrome" or AIDS. It has now been confirmed that the disease originates from the virus HTLV-III for which generally effective serological identification test procedures have now been devised including a rather primitive screening test of the ELISA type as well as the more specific "Western Blot". The virus up to now appears to be transmitted essentially exclusively through body fluids, particularly blood and semen; and its transmittal has been manifested primarily in homosexual males, hemophiliacs and drug addicts. However, extension of the disease outside these so-called "high risk" groups has more recently been observed including females as well as infants born to infected females, and there are in principle no fundamental constraints against its general dissemination. The annual rate of occurrence of the disease has increased alarmingly, although some reduction in the rate of increase seems to be currently the case. Nevertheless, the projected epidemiological impact of the disease is enormous with current projections in the order of several hundreds of thousands of patients; and the disease is, therefore, a potentially major epidemic threat. Various attempts have been made to treat the disease, and such treatment is currently the subject of intense medical investigation. As a disease, the symptomatic manifestation of AIDS is found at four different levels or stages. The least serious stage is the person who has been subjected to serological testing resulting in a positive indication for the AIDS virus but exhibits no other clinical symptoms. While available statistics and their analyses are limited, it appears that a certain percentage of this group can ultimately be expected to succumb to full-blown AIDS, while contrary to early predictions, a certain number may exhibit no further progression whatever for the remainder of their lives.

A second category contains persons having a positive serological test for the AIDS virus combined with a significantly measurable deficiency in the immunological function of their immunological defense systems. Tests are available for determining a reduction in immunological function below the normal standard which primarily involve comparison of the number of T-helper/inducer cells against the normal or average level of such cells in humans, and while these tests may not at their present degree of development permit precise quantification needed for accurate judgment of relative changes in immunological efficiency, they do reliably indicate whether the immunosystem of the person is or is not significantly impaired below normal levels.

The third group involves persons suffering from so-called "AIDS Related Complex" (ARC). These patients exhibit positive blood tests for AIDS virus, a depression in immunological function, together with other mild symptomatic effects which may include fever, night sweats, diarrhea, loss of appetite, fatigue, weight loss and the like. It appears approximately 7% of ARC patients will progress to a full-blown case of AIDS per year to an eventual total of 30–40%. Occasionally, sufferers from ARC will show improvement, but complete recovery is rare because the damage that has already been done to the immunological system remains irreversible with the necessary consequence of continued susceptibility to attack by external infection.

The final group are those clinically diagnosed as suffering from AIDS. The present clinical diagnosis for AIDS, as approved by the Federal Center for Communicable Disease Control in Atlanta is the combination of the following: (1) a positive serological test for the AIDS virus plus a loss in immune function, (2) identification in one of the high risk demographic groups specified above, and (3) the occurrence of either or both of Kaposi's sarcoma or a serious opportunistic infection usually necessitating hospitalization. Kaposi's sarcoma is a skin tumor generally purple in coloration with a slight dermal elevation that prior to the on-set of AIDS was practically never observed. Opportunistic infection, on the other hand, represents a disease caused by bacteria or fungi or viruses to which humans are constantly exposed but are normally effectively resisted by the unimpaired natural immuno-defense system. In particular, it includes otherwise rare forms of infection such as Pneumocystic Carnini Pneumonia, Avian Tuberculosis, Cryptococal Meningitis, Herpes Encephalitis, etc. to which humans are ordinarily resistant.

Generally, the first attack of the opportunistic infection can be successfully treated during hospitalization and the patient gradually recovers essentially completely from that attack and tends to feel generally well until a subsequent similar attack some months later, perhaps 9 to 12 months, which often proves fatal.

SUMMARY AND TECHNICAL CONTEXT OF THE INVENTIVE CONCEPT

According to the present invention, an essentially pure opiate or narcotic antagonist, i.e., which has the capability of blocking opiate receptors and thereby disabling such receptors from subsequent interaction with administered narcotics such as morphine and thereby suppressing the analgesic and euphoric action of the narcotic but without any corresponding action of its own, is effective at controlled dosages below ordinary narcotic-blocking amounts in the treatment of AIDS in its various clinical levels apparently through a remarkable and paradoxical inversion of its expected physiological behavior, resulting in a presumed potentiation of the action of endorphins in the body's immune system which for reasons that are not adequately understood lead to a definite improvement in the resistance of the immune defense system of the patient against the AIDS infection.

Endorphins are peptides generated in situ in the human body and are increasingly implicated by recent research in the mechanism of the body in dealing with acuate stress including pain relief enhanced immune function and reduced gastrointestinal activity. The term itself is a coined combination of endogenous and morphine, signifying a similarity in function but emphasizing the different source. Thus, the endorphins do indeed appear to at least simulate if not possess the characteristic analgesic and euphoric action of morphine, and they have been shown to share with morphine the same receptor sites, i.e., the elements of the body with which the drug interacts. It is also recognized that narcotic antagonists such as naloxone and naltrexone are as effective in blocking these receptor sites to endorphins as they are with respect to morphine. This blocking action of such antagonists is itself extraordinary since they are closely related chemical analogs of morphine, but the slight differences in chemical structure therebetween have profoundly different consequences on the effect of the respective drugs on the human system.

In the light of the blocking effect of narcotic antagonists against narcotics such as morphine, their principal medical utility up to now has, not surprisingly, been in the treatment of narcotic addiction and as antidotes against narcotic overdosage. Such utility has been recognized in the patent art in U.S. Pat. Nos. 3,254,008; 3,676,557 and 4,322,426, the second of which refers to an early opinion "that naloxone is a highly potent antagonist which is relatively free of side effects." However, contrary to this optimism, the actual side effects, while not major in any life threatening sense proved to be pronounced, including loss of appetite, irritability, sleeplessness, diminution of sexual drive, etc., and have unfortunately served as a deterrent against their ready acceptance by drug addicts, who were intended to be aided thereby. Hence, the initial promise of this group of drugs in dealing with the drug problem has not lived up to expectations.

Surprisingly, the same group of compounds, notably naloxone and naltrexone, have been proposed for medical purposes having little or no perceivable relationship with the treatment of drug addiction, or for that matter, with each other. Thus, in U.S. Pat. No. 4,181,726, naloxone at a dosage of 0.4–1000 mg at intervals of two to eight times a day, administered subcutaneously, is said to be effective in relieving the suffering from severe itching in conditions such as Hodgkins disease, mycosis funoides and severe jaundice and various forms of pruritis. Again, in U.S. Pat. No. 4,217,353 antagonists of this group are proposed for the treatment of anorexia at dosage levels in the range of 10–100 mg per day administered either orally or parenterally. According to U.S. Pat. Nos. 4,267,182 and 4,434,168, narcotic antagonists were found effective in the treatment of shock of all medical types including anaphylactic, burn, cardiac, neurogenic, etc., when administered by any of the various medically known routes at dosages in the range of 0.01–10 mg/kg animal body weight. Finally, this group of opiate antagonists is described in U.S. Pat. No. 4,388,324 for the treatment of alcoholism or as a counteractant against alcohol intoxication, in conjunction with other active ingredients, particularly certain linolenic acids and ascorbic acid.

Considering these diverse medical areas, the conclusion is inescapable that they have no perceivable relationship with AIDS, either as to etiology, physiological site, operative mechanism or any other recognizable factor. Furthermore, even if some common nexus were identifiable, any connection between the therapeutic action of narcotic antagonists for these medical purposes and AIDS would be far beyond even the most intuitive stretch of available medical evidence for the reason, if no other, of the critical dosage dependence of the medical efficacy of such drugs against AIDS. Without exception, these patents prescribe dosage levels of broad limits; whereas, for the treatment of AIDS these drugs must be utilized at minute levels quite different from those encountered in medical practice generally, with substantial higher levels resulting not only in a loss of such effectiveness but more likely in a destructive reversal in therapeutic result.

As far as is presently known, this dosage dependent effect of narcotic antagonists has been peviously appreciated by only one group of researchers but in a radically distinct medical situation. Thus, Zagon et al after demonstrating that the administration of Heroin to experimental mice injected with neuroblastoma, a sarcoma of the nervous system, prolonged the survival time and retarded tumor growth in such mice, went on to establish that the effect of the administration of naltrexone on mice similarly injected with neuroblastoma was highly dosage dependent. Thus, a single daily dose at a level of 10 mg/kg body weight proved to actually promote tumor growth and to decrease survival time, while a much reduced dose of the same drug at a level of 0.1 mg/kg body weight per day prevented development of that tumor in ⅔ of the injected mice and served to prolong the survival time in those developing the tumor. These researchers suggest that where the antagonistic blocking effect is intermittent rather than continuous, for instance as a result of a periodic dose too low to achieve continuous blockage, the number of opiate receptors can be increased which results in super-sensitivity to endorphins and enables the endorphinergic system to carry out its anti-tumor effect. In contrast, if the amount of the drug produces continuous blockage of the opiate receptors, endorphinergic modulation of tumor growth is inhibited. These experiments are discussed in the following papers:

Zagon, I.S., McLaughlin, P.J. Naloxone Prolongs the Survival Times of Mice Treated with Neuroblastoma. *Life Sci.*, 1981, Vol. 28, 1095-1102.

Zagon, I.S., McLaughlin, P.J. Heroin Prolongs Survival Time and Retards Tumor Growth in Mice with Neuroblastoma. *Brain Res. Bull.*, 1981, Vol. 7, 25-32.

Zagon, I.S., McLaughlin, P.J. Opioid Antagonist Inhibit the Growth of Metastatic Murine Neuroblastoma. *Cancer Letters*, 1983, Vol. 21, 89-94.

Zagon, I.S., McLaughlin, P.J. Naltrexone Modulates Tumor Response in Mice with Neuroblastoma. *Science*, 1983, Vol. 221, 671-672.

Zagon, I.S., McLaughlin, P.J. Duration of Opiate Receptor Blockade Determines Tumorigenic Response in Mice with Neuroblastoma: A Role for Endogenous Opioid Systems in Cancer. *Life Sci.*, 1984, Vol. 35 409-416.

Other workers have concluded that narcotic antagonists such as naloxone and naltrexone administered either in single doses or chronically provokes substantial increases in the number and sensitivity of opiate receptors which often persist for several days. See the following:

Tempel, A., Zukin R.S., Gardner, E.L. Supersensitivity of Brain Opiate Receptor Subtypes After Chronic Naltrexone Treatment. *Life Sci.*, 1982, Vol 31, 1401-1404.

Lahti, R.A., Collins, R.J. Chronic Naloxone Results in Prolonged Increases in Opiate Binding Sites in Brain. *European J. Pharmacol.*, 1978, Vol. 51, 185-186.

Zukin, A.S., Sugarman, J.R., Fitz-Syage, M.L., Gardner, E.L., Zukin, S.R., Gintzler, A.R. Naltrexone- Induced Opiate Receptor Supersensitivity. *Brain Res.,* 1982, Vol. 245, 285–292.

Shultz, R., Wuster, J., Herz, A. Supersensitivity of Opioids Following the Chronic Blockade of Endorphin Action by Naloxone. *Arch. Pharacol.,* 1979, Vol. 306, 93–96.

While the discoveries of Zagon et al are provocative, they have no recognizable connection with the treatment of AIDS as is evident from the simple fact alone that rodents have so far proven free of susceptibility to the AIDS virus, making an extrapolation between the different species out of the question even if the divergent nature of the disease in question were to be disregarded.

A profound result of this invention has been a determination that clinical improvement in symptomatic condition and apparent at least temporary enhancement in ongoing resistance to further progression of the disease in persons infected with the AIDS virus, by the low dose administration of an opiate antagonist is accompanied by, or perhaps causally linked with, a substantial reduction in the levels of serum or circulating alpha-interferon (hereinafter alpha-IFN) of a persistent nature. The existence of substantially elevated levels of alph-IFN, corresponding to acid-labile alpha-IFN, in a high majority of individuals clinically diagnosed with AIDS has already been established by several sources. See:

Preble, O.T., Rook, A.H., Quinnan, G.V., Vilcek. J., Friedman, R.M., Gelmann, E.P., Sonnabend, J.A. Role of Interferon in Aids. *Acquired Immune Deficiency,* I.J.-.Selikoff, A.S. Teirstein, S.Z. Hirschman, (Eds.) 1984, Annals N.Y. Acad. of Sci., Vol. 437, 65–75.

Buimovici-Klein, E., Lange, J., Klein, R.J., Grieco, N.H., Cooper, L.Z. Long Term Follow-up of Serum-Interferon and its Acid-Stability in a Group of Homosexual Men. *Aids Research,* 1986, Vol. 2, 99–108.

Specifically, Preble et al determine that in at least 70% of homosexual males suffering clinically from AIDS plus three hemophiliacs and two patients injected with AIDS via transfusion had substantially elevated levels of alpha-IFN. In contrast, the same researchers found significant levels of alpha-IFN in less than 2% of normal healthy individuals and in only 3 of 96 hemophiliacs. Somewhat elevated levels of alpha-IFN can be found in individuals suffering from colds and other respiratory diseases as well as in certain viral diseases but such elevation consistently declines to normal zero levels once the disorder has run its course. Similarly, when alpha-IFN is deliberately administered for therapeutic purposes with consequential exogenous increase in the serum levels thereof, such alpha-IFN is rapidly catabolized; whereas the observed elevated levels in AIDS patients persist virtually indefinitely.

Evidence exists that alpha-IFN is a strong endorphinergic agonist and a potency 800 times greater than morphine itself. See:

Dafny, N. Interferon Modifies Morphine Withdrawl Phenomena in Rodents. *Neuropharmacol.,* 1983, Vol. 22, No. 5, 647–651.

Blalock, J.E., Smith, E.M. Human Leukocyte Interferon (HuIFN-alpha): Potent Endorphin-Like Opioid Activity. *Biochem. Biphys. Res. Comm.,* 1981, Vol. 101, No. 2, 472–478.

It is generally accepted that opiate receptors, similar to other receptors, when subjected to strong agonistic action undergo a downward adjustment in their number and density, referred to as "down regulation", thereby reducing the ability of such receptors to participate in hemeostatic regulation of the immune defense system. Moreover, the possibility is conceivable that elevated alpha-IFN may result in a "false feedback signal", spuriously indicative of a reduced need for opiate receptor site formation, to either or both of the hypothalmus and anterior pituitary gland (which are associated with the endorphinergic system) and thereby interfere with the natural regulation action that might otherwise take place.

A definitive conclusion cannot be drawn from current data whether increased levels of alpha-IFN are a causative factor in the body's response to the AIDS infection by reason of a destructive action on certain components of the immune system or, alternatively, if the alpha-IFN is primarily a side effect of the infective mechanism of the AIDS virus. It is of interest that Preble et al found significantly elevated alpha-IFN levels in approximately 10% of homosexual men free at the time of clinical symptoms of AIDS, and similar elevations were discovered in blood samples of several patients drawn before they actually developed AIDS. The correlation between elevated alpha-IFN levels and the past or future onset of AIDS was sufficiently clear to lead these workers to propose the utilization of alpha-IFN levels as an indicator of the susceptibility of high risk individuals to later onset of the disease.

Therefore, the finding of a persistent and often progressively increasing reduction in alpha-IFN levels in a considerable majority of the clinically AIDS infected patients in the study underlying the present invention, is deemed to be of high importance in providing objective reproducible confirmation of a desirable alteration in the immunological condition of AIDS infected patients.

Alpha-IFN levels here are reported in terms of their "dilution values"; namely, the reciprocal of the largest number of dilutions performed serially, each at a reduction in concentration of one-half, necessary to bring the alpha-IFN concentration in a blood sample to an established reference level therefor in the standard "microtest" developed for this purpose and described by Preble et al, Annals N.Y. Acad. of Sci., supra, at pages 66 and 67. Such dilution levels are convergible into "international reference units" as there described, but since such conversion may not be consistent among all researchers, the dilution values themselves are specified here.

DETAILED DESCRIPTION OF THE INVENTION

The present invention depends upon the administration of an essentially pure opiate antagonist, preferably for Mu opiate receptors. Commercially available examples of essentially pure antagonists for Mu opiate receptors are the morphine derivatives naltrexone and naloxone. The effectiveness of these compounds for blocking opiate receptors is thoroughly documented in the literature, four of the five now known opiate receptor sites being at dosage levels substantially higher than in the present invention blocked thereby, including the Delta and Mu sites, the latter being recognized as the most sensitive to antagonist action. The development of new or experimental pure opiate antagonists is currently proceeding rapidly, and additional compounds useful in this method have already been discovered by such research or will certainly evolve therefrom. In general, based on present understanding, any opiate antagonist which is effective primarily against Mu opiate receptors and at the reduced dosages in question is essentially a pure Mu antagonist, i.e., exerts a selective blocking action for the Mu receptors exclusive of Delta receptors, could be employed at equivalent dosage levels. A number of drugs have been identified as possessing a combination of both agonistic and antagonistic properties. Such so-called "mixed agonists-antagonists" are not considered suitable for use here.

The preferred dosage of the essentially pure opiate antagonists employed in the present treatment is about 1.75–2.75 mg per patient per day daily for six days per week. However, a broader range of amounts of the active drug can be employed with more or less equal general effectiveness; and according to present understanding, the effective range extends between about 1 mg up to about 5 mg. This amount is based on naltrexone specifically, but equivalent amounts can be readily determined for other opiate antagonists which are essentially pure in their antagonistic action at very low dosage levels. Morphine is well recognized as a classical Mu agonist, and other antagonists than naltrexone can be readily standardized against morphine to quantify the amounts thereof that are equivalent to the effective dosage for naltrexone. For example, by means of tests evaluating the response of mice, the amount of morphine which is capable of being offset in its dependency effect by the desired amount of naltrexone can then be tested against other antagonists to determine the specific amount thereof necessary to produce the equivalent antagonist action against morphine as the naltrexone. For information concerning such tests, reference may be had, for example, to the text *Principles of Drug Action: The Basis of Pharmacology*, Goldstein et al, second edition, copyright 1974, John Wiley & Sons, at pages 604–609 in particular.

It is known that infants can suffer from AIDS, acquiring the disease by birth from an infected mother. The present invention is suitable for the treatment of infants and a recommended dosage level for such treatment is approximately 0.03 mg/kg of infant body weight. This dosage is generally equivalent to that recommended above for adults, being equal, for example, to about 2.1 mg for a male weighing 70 kg. Apart from the treatment of small infants, adjustment of the dosage level according to variations in weight of the patients being treated, for instance, females versus males, does not appear to be indicated; and, indeed, a reduced dosage level for adults of lesser weight might be contraindicated since a certain minimum concentration of the active antagonist in the system of the patient is likely essential for achievement of optimum improvement.

Naltrexone is the preferred antagonist employed in the present invention primarily by reason of its suitability for oral administration and is preferably administered in this way, e.g., in the form of capsules or tablets containing the proper dosage or as a solution or suspension in a suitable ingestible liquid carrier. A closely related analog of naltrexone, naloxone is used as an opiate antagonist in the treatment of narcotic overdose, and naloxone is consequently deemed to be also useful in the present invention. However, as presently available, naloxone is not suitable for oral administration and is short acting, so that it is less effective than naltrexone as the opiate antagonist employed in the present treatment method. Naloxone is known to be effective when administered by injection, i.e., either intravaneously, intramuscularly or subcutaneously, for the treatment of narcotic overdose and is available in forms appropriate for such administration and is consequently applicable in the present invention especially for patients unable to take medication by mouth. The potential exists for developing forms of naloxone for oral administration, and for such forms no such contraindications would exist. Obviously, the mode of administration selected for a particular essentially pure opiate antagonist should be one for which the antagonist is pharmacologically effective or active.

DESCRIPTION OF CLINICAL TRIAL

In order to test the effectiveness of the opiate antagonist of the present invention under practical clinical conditions, a clinical test was initiated according to a double blind protocol. The test originally covered a total of 59 male patients of which 57 were homosexuals or bisexuals, while the remaining two were drug addicts. Of the 59, 57 had been clinically diagnosed as suffering from AIDS, one was diagnosed as suffering from ARC, and the remaining patient was found to show a positive serological test for HTLV-III virus combined with significant immunodepression, i.e., a depressed T-helper cell count. An additional patient who was admitted in an extremely serious, i.e., pre-terminal, condition from AIDS, died almost immediately, and is not included. Any patients on narcotics or who had recently participated in any other medical studies were excluded.

Upon admission, the patients were randomly divided into two groups, based simply on sequence of admission. The clinical plan was to treat one group with the active opiate antagonist and the other group with a placebo for an initial three months (twelve weeks) test period after which, in view of the severity of the disease, all patients were to be given the active drug. Only the pharmacist in charge of dispensing the drug was informed as to the placement of the patients in the respective groups; neither the patients nor their medical personnel were informed of such placement until after the lapse of twenty weeks (several weeks following the inclusion of all patients on the active drug), at which point both patients and medical personnel were advised as to the original category of the patients. The only exception to this double blind protocal was in the case of patients developing a serious and potentially life threatening medical complication during the initial twelve weeks period; and for such patients, if they were initially included in the placebo group, they were switched to the active drug receiving group in the hope of forestalling a possibly fatal consequence. This occurred with five patients from the placebo group.

The opiate antagonist for administration purposes was dissolved in a heavy cherry syrup at a daily dosage of 1.75 mg, while the patients in the placebo group received the same syrup alone. The administered dose was compounded by the study pharmacist by grinding 50 mg naltrexone tablets, obtained under the tradename Trexan from the du Pont company, and dissolving several tablets in 3000 cc of a heavy cherry syrup. The syrup was dispensed in unit dose bottles, with 15 cc (containing 1.75 mg of the drug) in each bottle. Placebo patients were given the same bottles containing 15 cc of cherry syrup. Both active and placebo formulation were checked for possible differences, e.g., taste, by the staff, but none could be detected. The patients were instructed to take each dose orally six nights per week at bedtime or between 4:00 and 5:00 a.m., with the latter being preferred, the dosage to be omitted on the seventh night.

The study was conducted on an out-patient basis with the patients being seen weekly during the first three months of the test, then biweekly for four to eight weeks, and thereafter monthly. Upon admission and monthly thereafter, blood was drawn from each patient and subjected to various laboratory analyses. The latter included HTLV-III serology testing, T-cell subsets, SMA 16, urinalysis, CBC and differential, syphilis serology, and alpha interferon (alpha-INF). The tests for T-cell subsets, CBC, Diff, and alpha interferon were repeated monthly. A 30 cc syringe of heparinized blood was drawn monthly and frozen at 70° C., to be studied later for lymphocyte immune functions, viral cultures and a number of other relevant factors. The patients received a clinical evaluation by the physician or physician's assistant on each visit, using a research data collection form. This form inquired whether the patient during the preceding period had experienced any of the various symptoms often associated with AIDS, including nightsweats, anorexia, diarrhea, fatigue, coughing, shortness of breath, depression, and pain, their severity, if any, and in the case of pain its location and intensity. The patient was examined for Kaposi's sarcoma and where present the number of lesions thereof identified and roughly quantified. The occurrence of any infections was noted as well as the type, location and severity thereof. The occurrence of any nodes and their location was indicated. The mouth and pharynx were inspected, the chest was auscultated and any abnormalities noted, and the liver size was estimated. Any medication being taken by the patient was noted and inquiry was made as to the patient's general subjective evaluation of his sense of well being and life history during preceding period and these comments noted.

A patient was admitted to the study only after a telephonic conference with his physician, who continued to follow the patient throughout the trial, being consulted and advised by the staff when needed.

Nineteen of the original 59 dropped out of the study either immediately or before meaningful data could be accumulated and one died, leaving 39 on the trial (although data is not available for each one for all phases of the trial). Thus, 39 patients continued with the trial, of which 38 had AIDS in a clinical sense and one had ARC. Of the 38 with AIDS, 22 were diagnosed on the basis of Kaposi's sarcoma, 13 on the basis of a previous major opportunistic infection and 3 on the basis of both. The mean time interval between the date of diagnosis and entry into the trial was five months. All of the patients exhibited a significant depression in their immune systems with all but 5 having an absolute $T_4$ count at the time of admission of less than 400 ml, and the serum alpha-IFN level was 24 in one patient, 64 in three, 128 in twenty-five and 256 in eight. A level of serum alpha-IFN of 16 or higher is considered to be pathologically elevated.

Adequate data for the double blind period is available for 33 patients, of which 15 were in the active drug-receiving group and 18 were in the placebo group, the five seriously ill patients which switched from the placebo group not being counted in either group. Of the 18 placebo group members, two experienced a significant drop, apparently spontaneously, in alpha-IFN levels (i.e., a decrease to more than one-fourth the initial level, equivalent to two serial dilution in the standard microtest mentioned above). Of the 15 in the active group, seven experienced the significant drop in alpha-IFN during the double blind state.

As stated, the placebo group after the conclusion of the control stage, also received the active drug which eventually extended over a substantial period, e.g., at least four months, although necessarily for a lesser time than those initially present in the active group. Thus, a total of 39 patients were exposed to the drug for at least a four month period at some stage, for which adequate data is available for that period (but not necessarily for the entire trial in all cases). Of these 39 patients, 22 experienced the significant three-fourths or better drop in alpha-IFN level at some eventual time, and 17 patients did not exhibit that decrease at any time up to now.

As to the time period required for this reduction in alpha-IFN level in these 22 patients, this took anywhere from two to eleven months, and the mean time was 4.5 months. For several, the drop took place immediately, i.e., within the second month of treatment, and continued to fall. For others, an immediate drop was followed by fluctuations from the reduced level. A few required several months for the drop to take place. For still others, the drop was gradual or stepwise, following the inverse serial progression of the serial dilution technique, e.g., from 128 to 64, then to 32, next to 16 and on to normalcy. Currently, of the 22, 21 have an alpha-IFN level of 8, and 1 of 12.

The difference between a change in the first three months in 2 out of 18 patients of the placebo group and in 13 out of 29 (for which data is available) patients in the total drug-receiving group is statistically overwhelmingly conclusive.

As regards the clinical response of the patients to the instant treatment, their difference in condition is remarkable according to the effect on their alpha-IFN levels. Of the 22 having a drop in such level of at least three-fouths or better, 20 were alive and currently feeling well (with normal energy, appetite, weight, and no systemic symptoms), while one is ill.

One died of PCP while in the trial, and one not included in the 22 died three months after dropping out and discontinuing treatment. Furthermore, within this group four had mild episodes of PCP during the trial period, with three treated at home and all responding to antibiotics within 48 hours. In three of the four, these eipsodes occurred before any drop in alpha-IFN level had been detected. In striking contrast, of the 17 with no change in elevated alpha-IFN levels, 11 have died, and 4 are presently seriously ill, having developed major complications indicating serious progression of their disease. One of these four developed cytomegalovirus retinitis and polyneuritis and dropped out of treatment, one developed severe herpes encephalitis requiring several weeks of hospitalization, and remains with residual cerebral deficits, the third, the one patient with ARC, developed Karposi's sarcoma in his eighth month on the present treatment, changing his diagnosis from ARC to AIDS, and the last has developed a serious CNS disorder as yet not precisely diagnosed. One one patient with a consistently high IFN level is still doing well. Statistically speaking, the difference in death rate between the two groups (1/22 vs 10/15) is conclusively significant.

The unexpected resistance of the three patients from the drug receiving group to upper respiratory illness eventually, diagnosed as PCP enabling them to recover readily upon antibiotic treatment after about 24–48 hours, should not be overlooked. This particular form of pneumonia is characteristic of AIDS and is ordinarily a major life threatening illness for persons infected with AIDS, necessitating 3-4 weeks of hospitalization with a difficult clinical course notwithstanding intensive treatment. One of these three patients had previously undergone an episode of PCP prior to admission into the present trials and that eipsode had already been life threatening. As mentioned above, according to the normal progression of the AIDS disease, a subsequent episode of this particular type of pneumonia is ordinarily far more serious than the initial episode and is frequently fatal. The episode of this patient during the trials was characterized by only a mild cough, low grade fever and mild shortness of breath for three weeks which symptoms in fact were of such low grade nature that the condition was initially diagnosed as simply a mild upper respiratory illness. When the condition persisted, more detailed diagnostic procedures were applied including a bronchoscopy which resulted in the diagnosis of PCP and initiation of the treatment with an antibiotic which resulted in clearing of the symptoms in less than 48 hours. Another of these three patients had likewise experienced a prior episode of PCP before inclusion in these trials with a similar difference in severity and treatment effectiveness.

As stated, all of the patients in the trial with the one noted exception had AIDS in the clinical sense and were randomly grouped without regard to the severity or intensity of the disease at the time of admission. In any event, it is difficult if not impossible to characterize the progression of the AIDS disease after diagnosis so that the particular status of the disease for the respective patients was in any case unknowable. At the present state of understanding of AIDS, no patient diagnosed for AIDS has ever been "cured". The average life span post diagnosis is eighteen months. It is believed that the present treatment, despite a too-short duration for the accumulation of definitive evidence, will result in a core group of AIDS patients who will survive and will undergo a gradual healing of their AIDS-damaged immune systems until they eventually are restored to substantial normalcy.

Proof of this conclusion will itself be complicated by the absence of any available diagnostic procedure for quantifying damage to the immune system. At present, the function of the human immune system is determined by counting the number of T-helper cells found in the blood, but this count is subject to such wide inherent variations that the principal value of the test is simply as a positive or negative indication of immune system impairment but not as a measure of the relative extent or degree of such impairment.

For the reasons explained above, it is not possible to identify any specific point in the course of the AIDS disease for a specific patient due to inadequate diagnostic techniques, and consequently, it is impossible now to state definitively how the disease develops in the human system. It seems likely, however, that it depends upon a pattern of flow and ebb in which the virus first attacks and then is repulsed by the immune system temporarily, then attacks more vigorously and possibly repulsed once more, and then eventually simply overwhelms the immune defenses leaving the patient completely vulnerable to the onset of infection without any of the natural resistance to the course of that infection which results in death. The present invention appears to function by enhancing the immune function of the patient's natural immune system, possibly due to the reduction or removal of the alpha-IFN. Therefore, the enhanced immune system of the patient acquires sufficient resistance against the onslaught of the virus and secondary infections until it is enabled to bring the viral population under control.

What is claimed is:

1. A method of treating humans infected with HTLV-III (AIDS) virus, which comprises the steps of administering by a pharmacologically effective mode to such patient an effective dosage within a range corresponding to about 1.0 to about 5.0 mg for naltrexone, of an essentially pure opiate receptor antagonist which within said dosage range exerts an opiate receptor blocking action substantially exclusively towards Mu opiate receptors.

2. The method of claim 1 wherein said dosage is administered substantially between the hours of 9:00 p.m. and 5:00 a.m. in order to achieve substantially enhanced effectiveness in releasing endorphins into the system of the human being treated.

3. The method of claim 2 wherein said dosage is administered generally between the hours of 2:00 and 5:00 a.m.

4. The method of claim 1 wherein said opiate receptor antagonist is either naltrexone or naloxone.

5. The method of claim 1 wherein said virus infection is indicated by a positive serological test for said virus.

6. The method of claim 1 wherein said human being treated is suffering from a clinically diagnosed case of AIDS.

7. The method of treating humans infected with HTLV-III (AIDS) virus which comprises the step of administering by a pharmacologically effective mode to such patient an effective amount of an essentially pure opiate receptor antagonist which is sufficient to exert an opiate receptor blocking action against Mu receptors but insufficient to exert such action against Delta receptors.

* * * * *